United States Patent
Pressly, Sr. et al.

(10) Patent No.: US 6,942,652 B1
(45) Date of Patent: Sep. 13, 2005

(54) RETRACTABLE I-V CATHETER PLACEMENT DEVICE

(75) Inventors: William B. S. Pressly, Sr., Greer, SC (US); John M. Mitnick, Atlanta, GA (US)

(73) Assignee: MedSafe Technologies, LLC, Lawrenceville, GA (US)

(*) Notice: Subject to any disclaimer, the term of this patent is extended or adjusted under 35 U.S.C. 154(b) by 0 days.

(21) Appl. No.: 10/648,032

(22) Filed: Aug. 26, 2003

Related U.S. Application Data

(63) Continuation of application No. 09/502,372, filed on Feb. 11, 2000, now Pat. No. 6,620,136.

(60) Provisional application No. 60/120,622, filed on Feb. 15, 1999, provisional application No. 60/138,414, filed on Jun. 8, 1999.

(51) Int. Cl.[7] ............................................. A61M 5/178
(52) U.S. Cl. .................................. 604/508; 604/164.08
(58) Field of Search ..................... 604/164.01, 164.08, 604/187, 189, 192, 198, 201, 508

(56) References Cited

U.S. PATENT DOCUMENTS

| | | |
|---|---|---|
| 4,772,265 A | 9/1988 | Walter |
| 4,834,718 A | 5/1989 | McDonald |
| 4,892,521 A | 1/1990 | Laico et al. |
| 5,176,650 A * | 1/1993 | Haining .................. 604/164.08 |
| 5,205,829 A * | 4/1993 | Lituchy .................. 604/164.08 |
| 5,211,629 A | 5/1993 | Pressly et al. |
| 5,215,528 A | 6/1993 | Purdy et al. |
| 5,336,187 A | 8/1994 | Terry et al. |
| 5,356,390 A | 10/1994 | Erskine |
| 5,462,533 A | 10/1995 | Daugherty |
| 5,545,146 A | 8/1996 | Ishak |
| 5,562,634 A | 10/1996 | Flumene et al. |
| 5,613,952 A | 3/1997 | Pressly, Sr. et al. |
| 5,683,368 A | 11/1997 | Schmidt |
| 5,690,619 A | 11/1997 | Erskine |
| 5,700,250 A | 12/1997 | Erskine |
| 5,800,403 A | 9/1998 | Pressly, Sr. et al. |
| 5,846,227 A * | 12/1998 | Osterlind ............... 604/164.08 |
| 6,010,487 A | 1/2000 | DeMichele et al. |
| 6,074,370 A | 6/2000 | Pressly, Sr. et al. |
| 6,156,015 A * | 12/2000 | DeMichele et al. ......... 604/263 |
| 6,179,812 B1 * | 1/2001 | Botich et al. ............... 604/110 |
| 6,213,978 B1 | 4/2001 | Voyten |
| 6,613,002 B1 * | 9/2003 | Clark et al. ................. 600/593 |
| 6,620,136 B1 | 9/2003 | Pressly, Sr. et al. |

* cited by examiner

Primary Examiner—J. Casimer Jacyna
(74) Attorney, Agent, or Firm—J. Bennett Mullinax, LLC

(57) ABSTRACT

An intravenous catheter placement device having a hollow body and a nose on one end of the hollow body. A needle hub fits within the nose and contains a needle embedded therein. A catheter is free to slide along the needle and substantially covers the shaft of the needle. Winged beams on the needle hub include catches and release tabs that cooperate with slots in the nose to retain the needle hub in the nose. A magnified transparent verification cavity in the needle hub provides for viewing blood flash in the cavity to verify that the intravenous catheter is inserted into the correct location. An energy storage device in contact with the needle hub releasably retains the needle hub to prevent premature projection of the needle hub into the hollow body. Upon insertion of the intravenous catheter and introducer needle into a patient, depressing the release tabs triggers the needle hub and blunts the needle within the catheter and projects the needle hub and embedded needle into the hollow body.

12 Claims, 21 Drawing Sheets

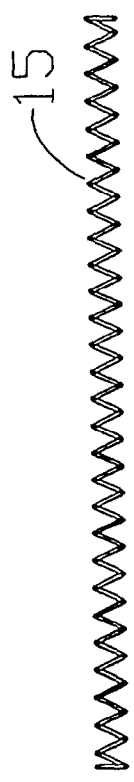
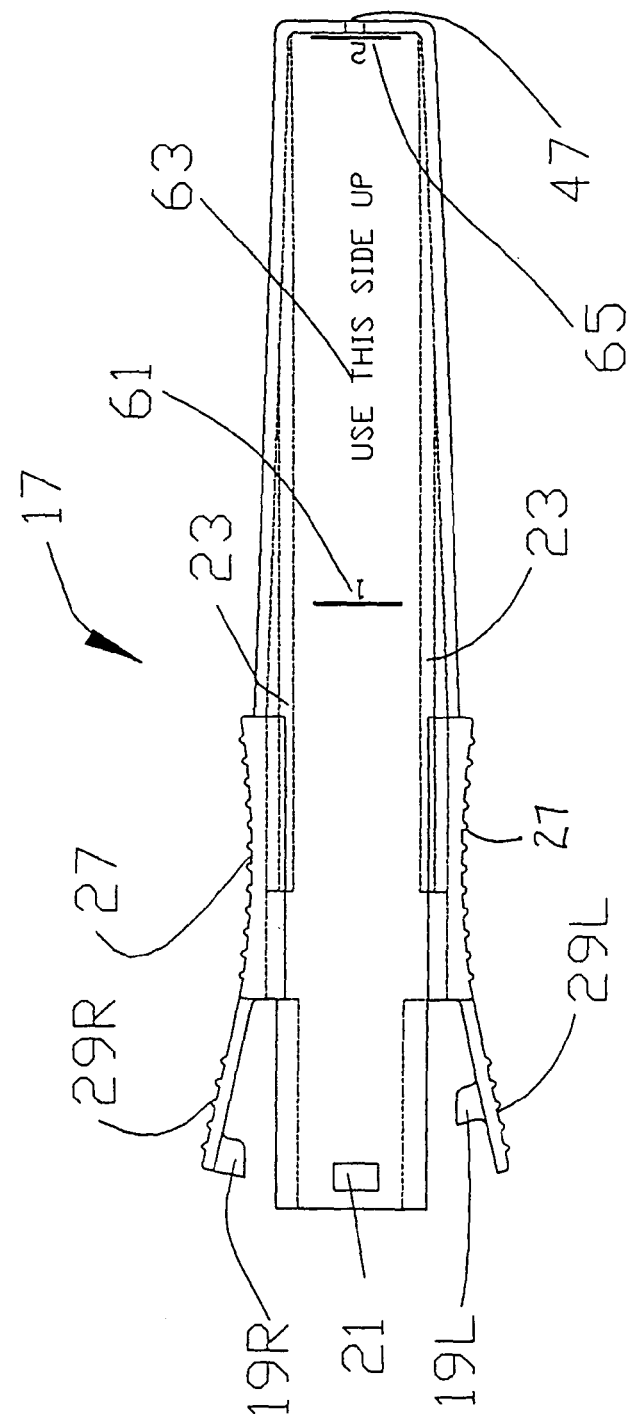
FIG 5
FIG 6

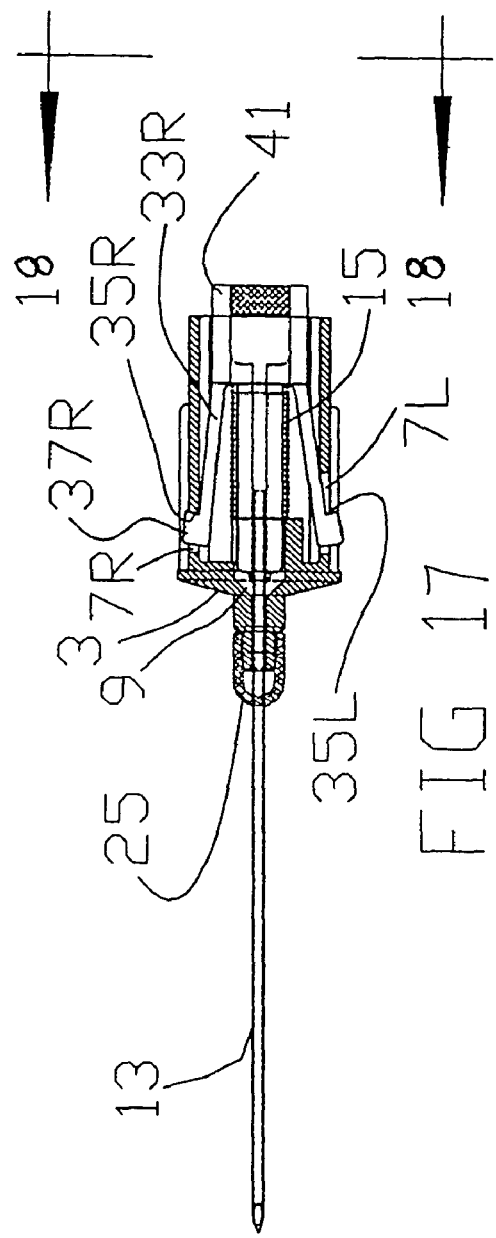
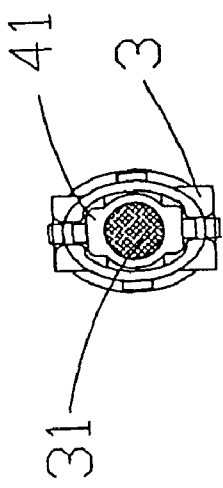
FIG 17
FIG 18

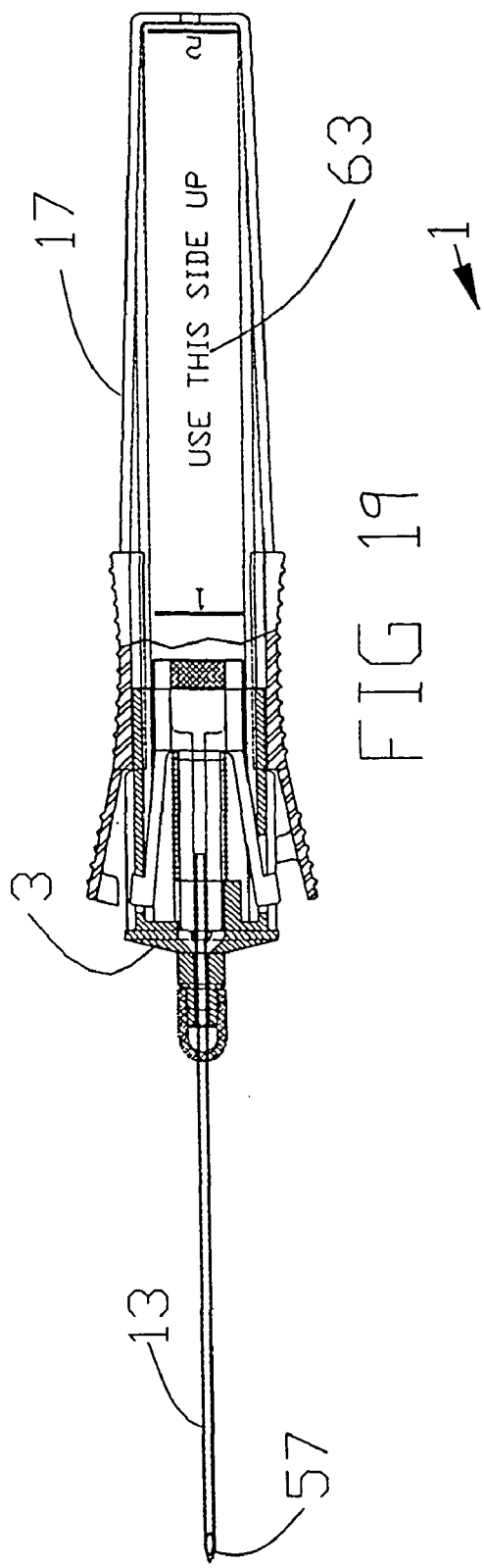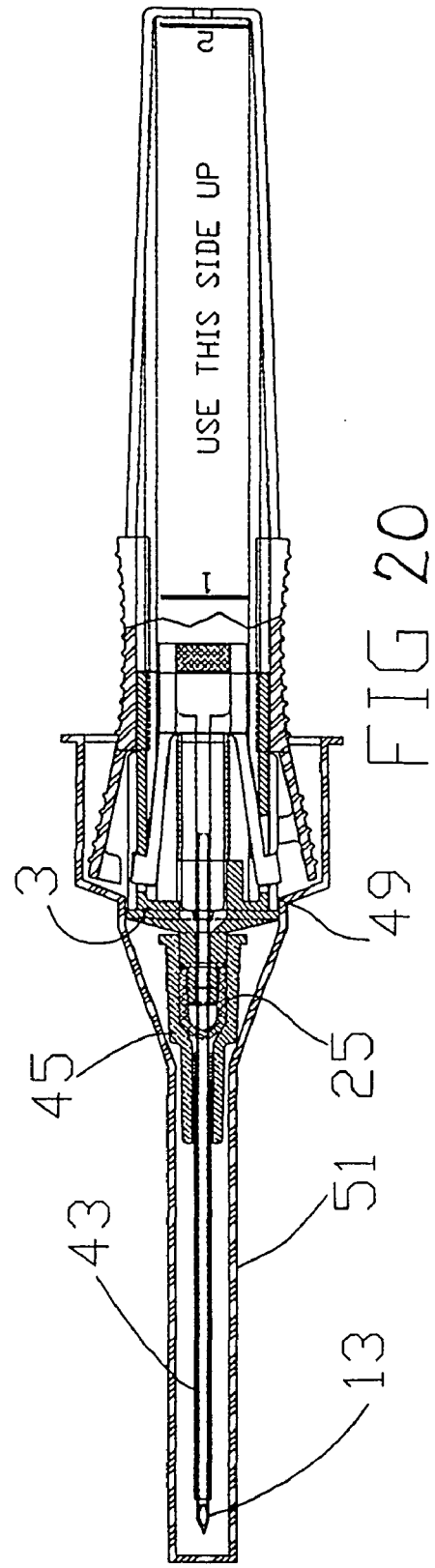

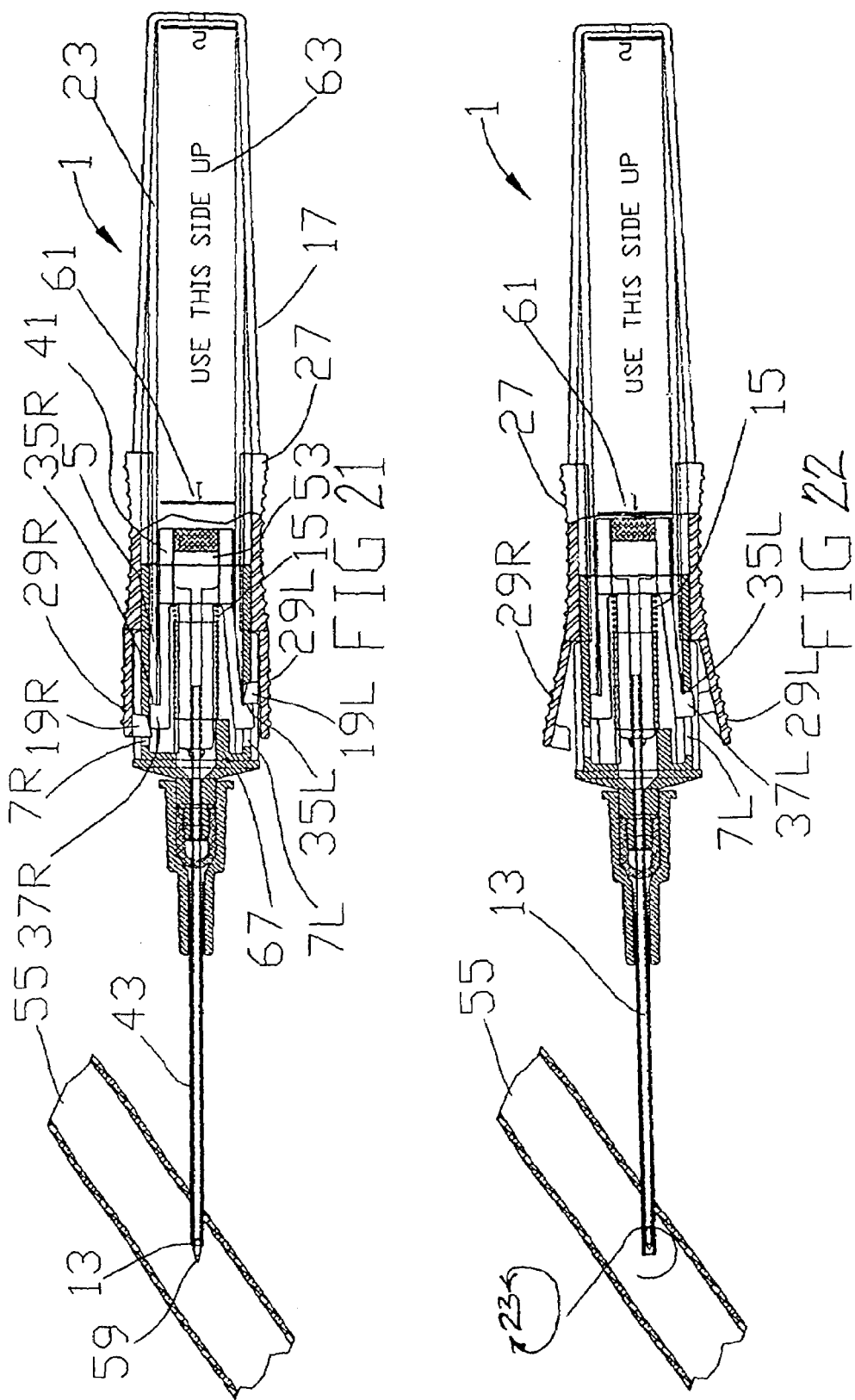

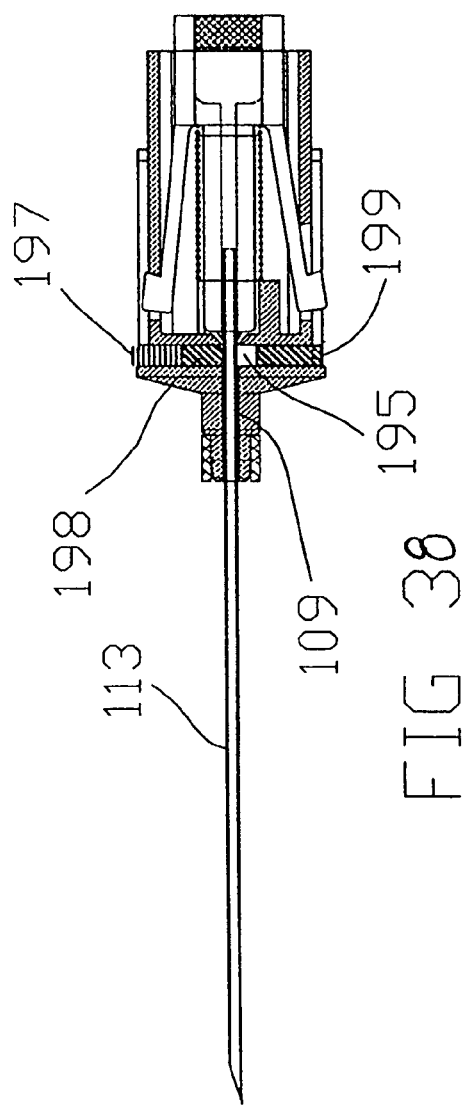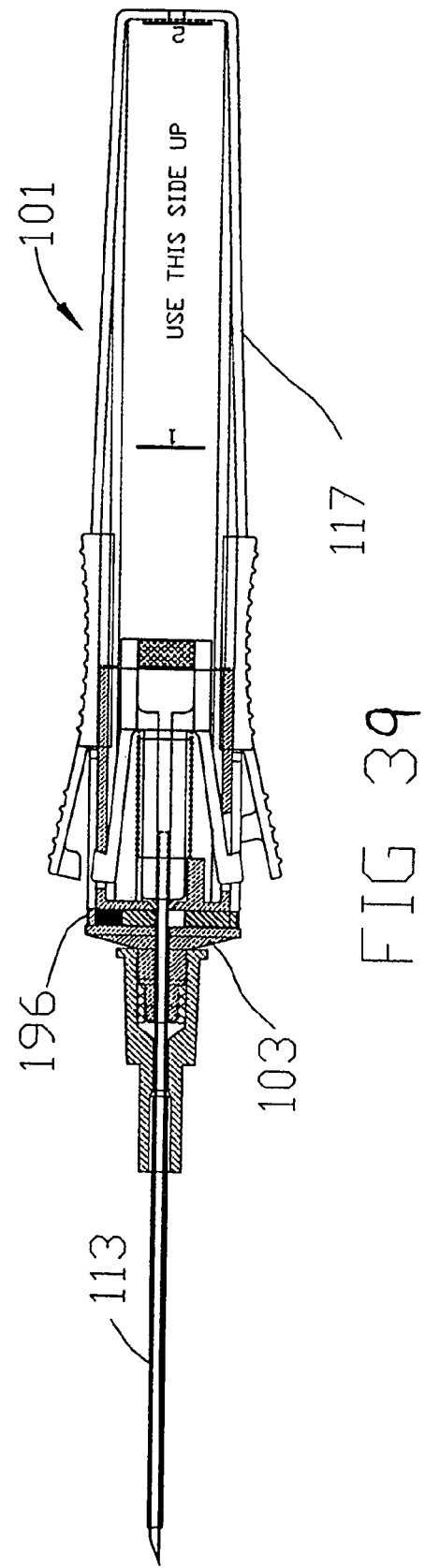

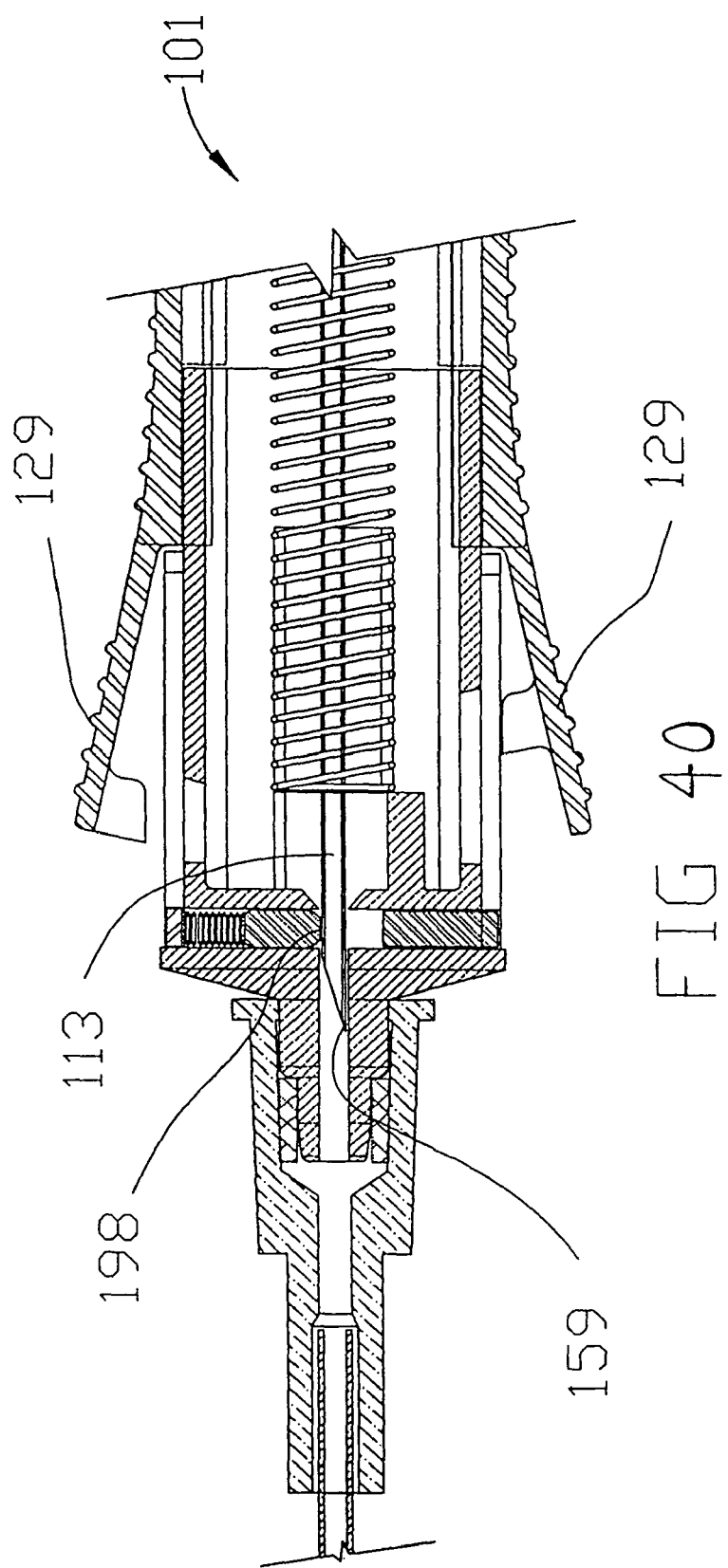

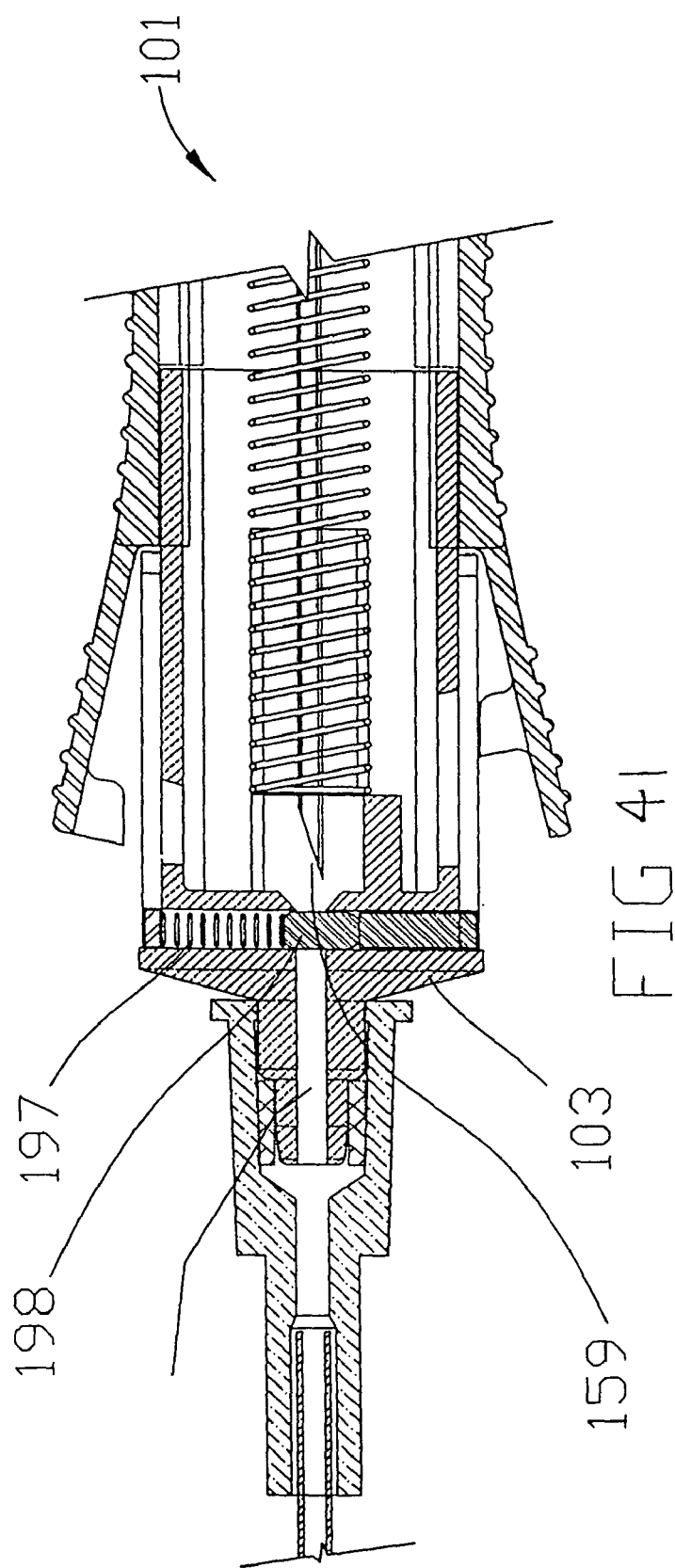

RETRACTABLE I-V CATHETER PLACEMENT DEVICE

RELATED APPLICATIONS

This application is a continuation of Ser. No. 09/502,372, filed Feb. 11, 2000, now U.S. Pat. No. 6,620,136.

This application claims priority to U.S. Patent Applications No. 60/120,622 filed Feb. 15, 1999, entitled "Retractable I-V Catheter Injection Device," and No. 60/138,414 filed Jun. 8, 1999, entitled "Retractable I-V Catheter Injection Device," which are incorporated by reference herein.

BACKGROUND OF THE INVENTION

This invention relates generally to intravenous (I-V) catheter placement devices that reduce the likelihood of accidental needlestick injuries. In recent history, preventing the transmission of contagious diseases, particularly those brought about by the co-mingling of human body fluids, has been of great technological interest. One of the particular problems has been associated with the use and disposal of I-V catheter introducer needles by health care workers. There have been various devices developed for the destruction of the introducer needles or cannula used with I-V catheters. Additional devices have been developed for the capping or hooding of I-V catheter introducer needles, all of which attempt to minimize the likelihood of needlestick injuries to health care workers and others after the needles have been used. The accidental puncture or pricking of a finger, or any other part of the body, after the treatment of a patient with a contagious disease, particularly a deadly contagious disease, results in a high likelihood of transmission of blood borne pathogens and the associated disease.

SUMMARY OF THE INVENTION

It is thus an object of this invention to provide an I-V catheter placement system which minimizes the likelihood of accidental needlestick injuries.

It is a further object of this invention to provide such an I-V catheter placement device which, after utilization with a patient, captures, encapsulates, and isolates the used needle so as to render such needle harmless.

It is a further and more particular object of this invention to provide such an I-V catheter injection device that has two stages of needle isolation, which provides magnification of blood "flash-back" in the device, which provides blood flow restriction, and which is operable utilizing only one hand which remains always behind the tip of the needle during the operation of the device and its safety features.

It is a still further object of the invention to provide a simple device which is manufacturable in high volumes.

These as well as other objects are accomplished by an I-V catheter injection device having a hollow body or barrel, with a nose attached to one end of the body and closed at the opposite end. The nose is disposed to the interior of said hollow body through a passageway, integral to the nose.

One end of a hollow needle, which is embedded in a hollow and transparent needle hub, is controlled in the passageway within the nose by a shaft appendage of the needle hub, and is in contact with energy storage means such as a spring, placed into the passageway ahead of the needle hub shaft. The other end of the needle passes through the spring and the passageway, and protrudes through boot (which may be elastic or rigid) that is attached to the nose of the catheter injection system. Covering the exposed shaft of the needle, while leaving the point of the needle exposed, is a thin wall concentric sleeve, or catheter, which is free to slide completely along the distal end of the needle. The needle hub shaft, onto which the opposite, proximal end of the needle is attached, is fixed to a transparent needle hub. The needle hub has two symmetrical winged beams, which are cantilevered from the back of the needle hub in the direction of the needle hub shaft and project at an angle away from the needle hub shaft and needle hub.

The geometry of the distal end of each winged beam is defined with angled catches for fixing the needle hub, with the spring in contact with it, into retainer slots in the sidewall of the nose. On the adjacent side of each catch is a release contact point for operationally releasing the needle hub from retainer slots during retraction of the needle and needle hub into the body of the device during use of the device. In an assembled state, the needle hub is held by one of the catches on the winged beams in position in the nose against the spring and ready for use. The opposite catch floats in its nose slot, which is slightly longer than the first nose slot, until actuation of the retraction cycle.

Use of the I-V catheter placement device is accomplished by holding the device at the finger grips in one hand with the orientation message "USE THIS SIDE UP," inscribed on the body of the device, visible to the clinician and with the needle pointing away from the clinician. The injection site of the patient is held with the other hand, such that the second hand is behind the needle at all times and is thus shielded from possible accidental needlestick. The introducer needle, with the catheter, is then injected part way into the patient's vein at the desired location, such that just the tip of the needle and catheter have been inserted. The clinician then receives visual verification of proper veinal placement of the needle and catheter by observing the appearance of blood "flash-back" in the inner cavity of the needle hub (which is magnified).

When proper entrance of the needle and the catheter tip into the patient's vein is confirmed, two release tabs on the sides of the body of the device are simultaneously depressed and released, causing the needle tip to retract just inside the tip of the catheter. As the needle and needle hub retract, visible indication of such retraction is provided to the clinician, whereby the needle hub is stopped at a fixed reference line on the body labeled as "1". In addition, audible indication of such retraction is provided by a "clicking" sound which is audible when the release tabs are depressed, and again when they are released. With the needlepoint effectively blunted inside the tip of the catheter, complete insertion of the catheter is then accomplished by the user without risk of the needle tip piercing the backside of the vein and thus "blowing the vein."

Once the catheter is properly inserted into the patient's vein, the two release tabs on the sides of the body are again simultaneously depressed and released. This action releases the remaining needle hub catch from its slot in the nose, and the needle hub with the needle attached thereto, is projected by stored energy in the spring (or other energy storage means) into and retained within the body of the device. Visible verification of such needle retraction is provided to the clinician by him or her observing that the needle hub is positioned at a second fixed reference line at the back of the body of the device labeled as "2." In addition, audible indication of such retraction is provided by a "clicking" sound which is audible when the release tabs are depressed. As the needle tip passes the boot at the nose of the device, the hole in the boot through which the needle has passed closes, and blood flow from the catheter into the body of the device is restricted.

External blood flow from the device is further restricted by the sealing action between the boot and the internal wall of the catheter head. With the needle safely contained within the body of the device, the clinician applies digital pressure at the entry point of the catheter into the patient's body to block blood flow from the catheter, removes the body of the device (which acts as a plug in the catheter head), and inserts the I-V line into the catheter head. Digital pressure is then removed, completing the process. An alternative embodiment of this invention provides for sequential depression of the individual release tabs to actuate needle retraction.

An alternative embodiment of this invention provides a second method of automatically plugging the nose of the device for flow restriction and added needle security.

BRIEF DESCRIPTION OF THE DRAWINGS

FIG. 5 is an elevational side view of the spring of this invention.

FIG. 6 is a top view of the barrel of the device shown in FIG. 1.

FIGS. 15–20 illustrate the assembly of the device shown in FIG. 1.

FIGS. 21–27 illustrate the operation of the device shown in FIG. 1.

FIGS. 37, 38 and 39 illustrate assembly of the alternative embodiment from the parts illustrated in FIGS. 28–36.

FIGS. 40, 41, and 42 are partial, longitudinal sectional views illustrating the operation of the alternative embodiment of the catheter placement device of this invention shown in FIGS. 28–39.

DETAILED DESCRIPTION

This invention provides an I-V catheter placement device operable with one hand and having a two-stage needle retraction mechanism using one set of release tabs. The first stage of retraction effectively blunts the needle tip and allows insertion of the full length of the catheter without risk to the patient, while the second stage of retraction fully retracts the needle hub, with its contaminated introducer needle attached, harmlessly into the body of the catheter placement device where it is captured and encapsulated, thus protecting the clinician from an accidental needlestick injury.

Once encapsulated inside the body of the catheter placement device, there is no risk of accidentally pricking or poking human tissue, thus minimizing the likelihood of transfer of blood borne pathogens which may be carried by fluids contained on the surface of or within such needle. Other advantages and features will become apparent from the following description and reference to the Figures.

Figure 1:
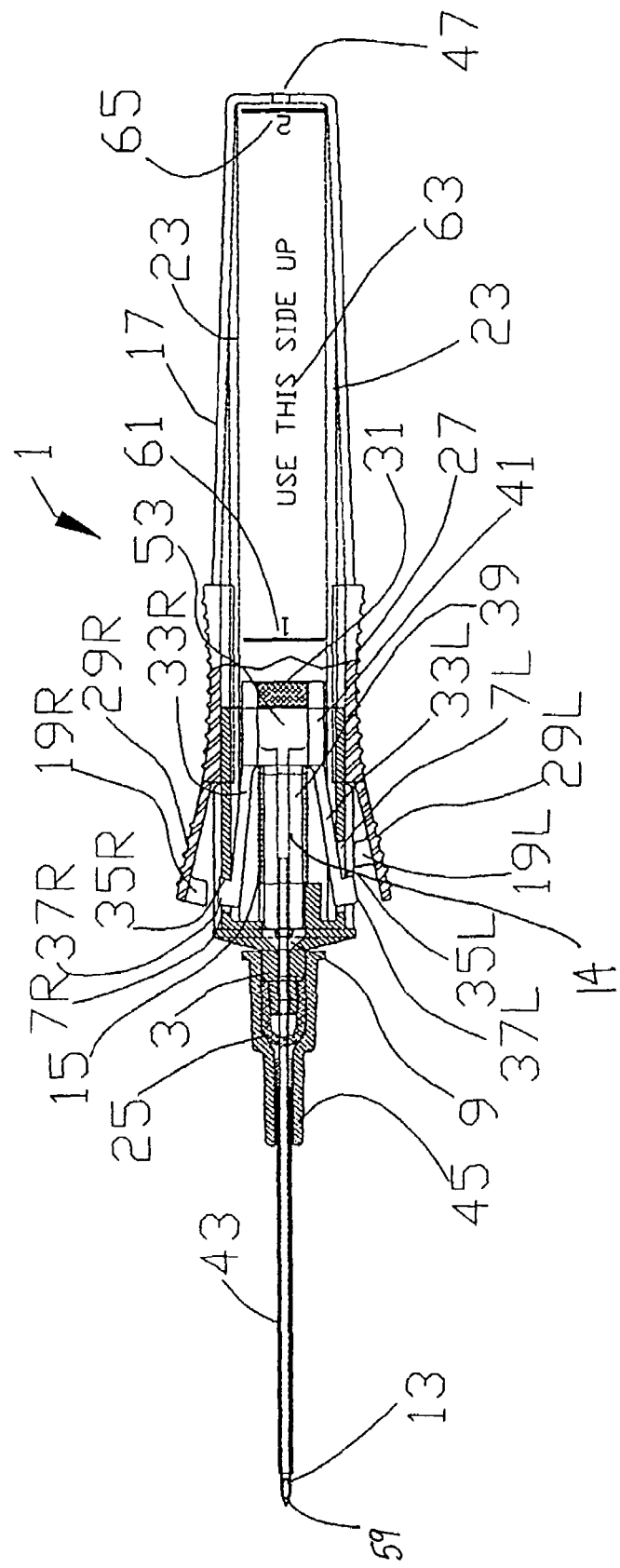
FIG. 1 is a longitudinal cross-sectional view of the I-V catheter placement device of this invention in its operable state with the needle, or distal end, on the left.
Figure 2:
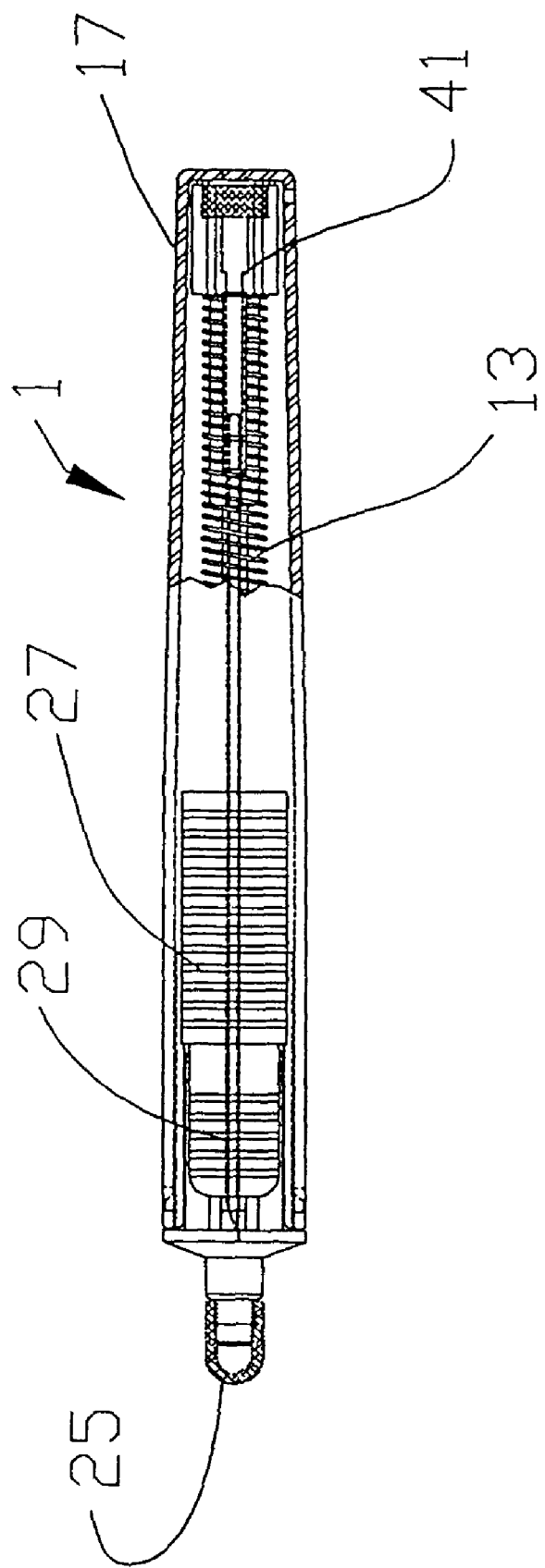
FIG. 2 is a longitudinal cross-sectional view of the I-V catheter placement device shown in FIG. 1 in its post operational state.

FIGS. 1 and 2 illustrate the catheter placement device 1 of this invention with the needle 13 and catheter 43 in its normal pre-injection position. FIG. 2, however, shows the final position of the needle 13 after operation of the retraction cycle so that the needle hub 41 (with needle 13 attached) is held in hollow catheter body 17 and rendered harmless after the placement of the catheter 43 has taken place. The I-V catheter placement device 1 has relatively few components.

Referring to FIG. 1, I-V catheter placement device 1 has a hollow barrel or body 17 with a nose 3 attached to one end. Barrel 17 is closed at the opposite end. A passageway 9 through nose 3 communicates with the interior of the hollow barrel 17. A proximal end of hollow needle 13 is fixed in a through hole 14 of needle hub shaft 39, which is in communication with a magnified blood "flash-back" verification cavity 53 in needle hub 41. Membrane 31 is positioned in the verification cavity 53 remote from needle 13 to allow airflow through membrane 31 but to prevent flow of blood into hollow barrel 17 as the catheter is inserted into a patient's vein.

Needle hub 41 is controlled in the passageway 9 within the nose 3 by needle hub shaft 39, and is in contact with spring 15, which is compressed into the passageway 9 ahead of needle hub shaft 39. The distal end of the needle 13 passes through spring 15, passageway 9, and nose boot 25 and protrudes from the nose end of the catheter injection system 1. Covering the exposed shaft of the needle 13, while leaving the point of the needle 13 exposed, is a thin wall concentric sleeve, or catheter 43, which is free to slide completely along the distal end of needle 13. Catheter 43 is fixed to nose 3 at catheter head 45 by light friction between catheter head 45 and nose boot 25 which provides a liquid tight seal between the catheter head 45 and nose boot 25 and also makes them easily separable during use.

Needle hub shaft 39, into which is fixed the proximal end of needle 13 in a through hole 14 running the length of shaft 39, is an appendage of needle hub 41. Needle hub 41 has winged beams 33R and 33L which are cantilevered from the back of the needle hub 41 in the direction of the needle hub shaft 39 and project at an angle away from needle hub shaft 39. The geometry of the distal end of winged beams 33R and 33L is defined with an angled catch 35R for coupling the needle hub 41, with spring 15 in contact therewith, into retainer slot 7R in the side wall of nose 3. On the adjacent side of catch 35R is a release contact point 37R for operationally releasing needle hub 41 from retainer slot 7R through the application of force during retraction of the needle 13 into the body 17 during use. In its pre-activated retraction state, spring 15 urges needle hub 14 away from nose 3. However, needle hub 41 is held by angled catch 35R on winged beam 33R in its position in passageway 9.

Use of I-V catheter placement device 1 is accomplished by holding the catheter placement device 1 at its symmetrical finger grips 27 in one hand such that orientation message 63 "USE THIS SIDE UP" is readable by the clinician, with needle 13 pointed away from the clinician. The placement site of the patient is held with the other hand, such that the second hand is behind the needle at all times and is intrinsically protected from possible needlestick by the patient's body. The tip or point 59 of needle 13, with the catheter 43, is just placed into the patient at the desired location. Verification of correct location of the catheter 43 is obtained by clinician observation of blood flash-back into magnified transparent verification cavity 53 in needle hub 41. Once proper location is confirmed, release tabs 29R and 29L are simultaneously depressed two times a) effectively to blunt the needle tip, and b) to retract needle 13 into the body of catheter 17.

As may be seen in FIG. 2 and FIG. 1, actuation of the catheter placement device 1 retraction cycle occurs when release tabs 29R and 29L, just in front of finger grips 27 of the catheter placement device 1, are simultaneously depressed. When this occurs, force is applied by contact pads 19R and 19L on the interior surfaces of release tabs 29R and 29L to release contact points 37R and 37L on the winged beams 33R and 33L of the needle hub 41. As force is applied, inward movement of catches 35R and 35L in their respective retaining slots 7R and 7L occurs, and catches 35R and 35L, holding the needle hub 41 into its cocked position, are subsequently released in two sequential depressions of release tabs 29R and 29L. As catch 35L releases from retainer slots 7L, there is nothing to restrain needle hub 41, and needle hub 41 is triggered, allowing energy stored in spring 15 to be released, projecting needle hub 41 with its embedded needle 13 towards the closed end of barrel 17. Once needle hub 41 is released, it is guided by channels 23 on an interior of the barrel 17 towards the closed end of barrel 17. Needle hub 41 is prevented from escaping from the interior of the barrel 17 by residual force from spring 15.

FIGS. 3 through 10 more particularly illustrate the components of I-V catheter placement device 1.

Figure 3:
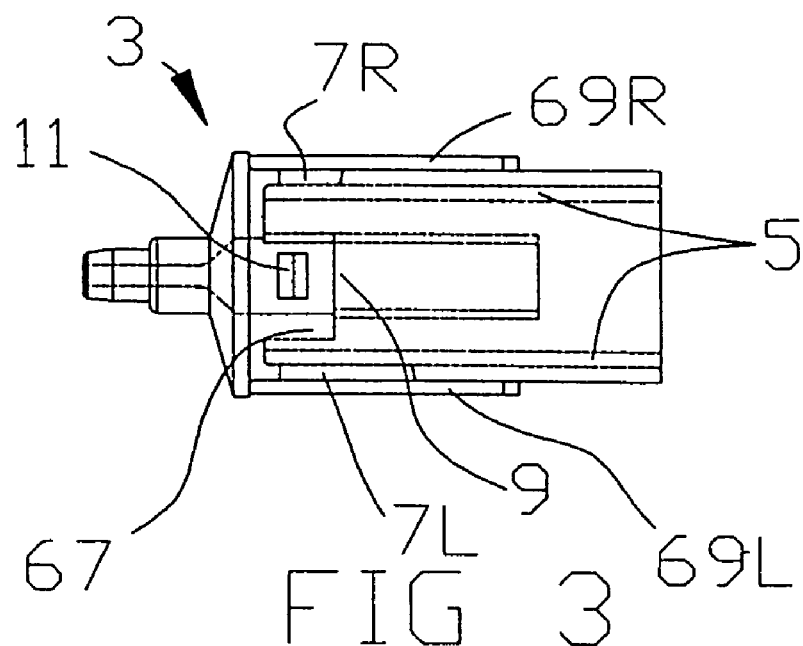
FIG. 3 is an isolated top view of the nose of the catheter placement device shown in FIG. 1.

FIG. 3 is an isolated top view of nose 3 showing passageway 9. Retainer slots 7R and 7L which lock the needle hub 41 into its operational positions are also shown. Longitudinal grooves or channels 5 guide the needle hub 41 in the nose 3 during the retraction cycle, and stop 67 helps capture catch 35L during the first stage of needle retraction of needle hub 41.

Figure 4:
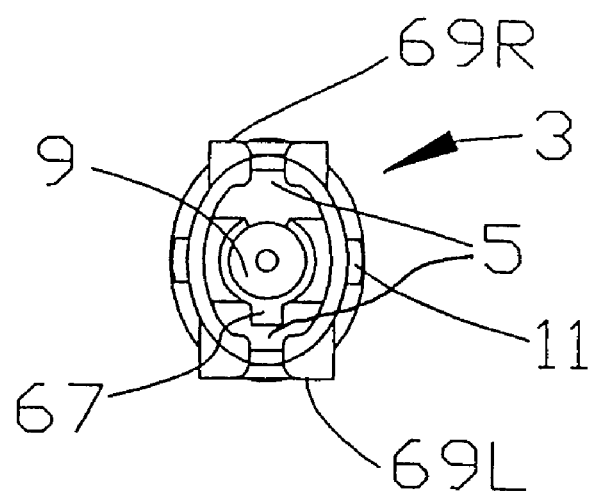
FIG. 4 is a proximal end view of the nose shown in FIG. 3.

FIG. 4 is proximal end view illustrating nose 3 of this invention and showing the channels 5 and tabs 11. Tabs 11 are used to attached the nose 3 to body 17.

FIG. 5 is an elevational view of the spring 15.

FIG. 6 is a top view of body 17. Release tabs 29R and 29L project from symmetrical finger grips 27, and slots 21 on both the top and bottom sides of the body 17 receive tabs 11 when attaching the nose 3. Contact pads 19R and 19L on the interior surfaces of the release tabs 29R and 29L cooperate with release catches on the needle hub. Also illustrated in this view are channels 23 which guide the needle hub 41 in the body 17 during retraction of needle hub 41, and the orientation message "USE THIS SIDE UP," with two reference lines labeled as "1" and "2" to show the positions of the needle hub during both stages of needle retraction.

Figure 7:
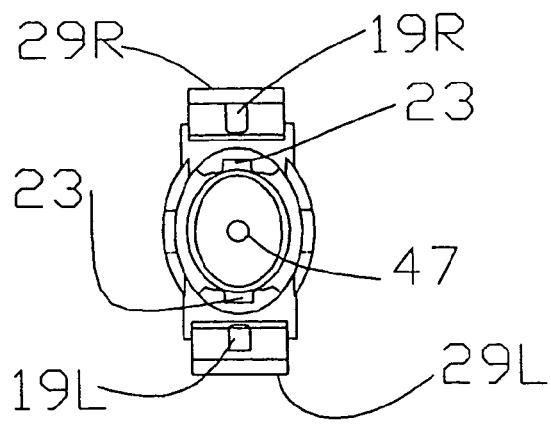
FIG. 7 is a distal end view of the barrel shown in FIG. 6.

FIG. 7 is a distal end view of body 17, illustrating release tabs 29R and 29L, channels 23, and contact pads 19R and 19L, and air release hole 47 in the proximal end of barrel 17.

Figure 8:
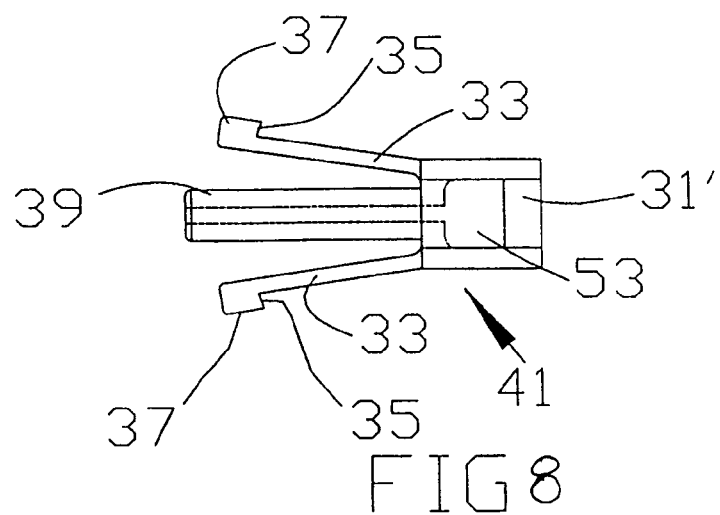
FIG. 8 is a side view of the needle hub of the device shown in FIG. 1.

FIG. 8 is a side view of needle hub 41 illustrating the space 31' for membrane 31, transparent verification cavity 53, winged beams 33, catches 35, release contacts 37 and the needle hub shaft 39 projecting between winged beams 33.

Figure 9:
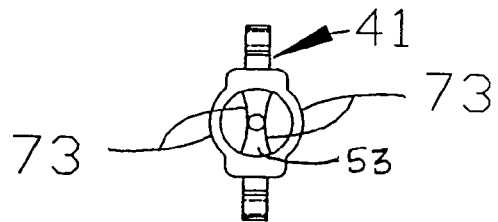
FIG. 9 is proximal end view of the needle hub shown in FIG. 8 well illustrating the magnification surfaces of the needle hub.

FIG. 9 is a proximal end view of needle hub 41 showing magnification surfaces 73 of verification cavity 53 that act as lenses to make the presence of blood in cavity 53 easier to determine.

Figure 10:
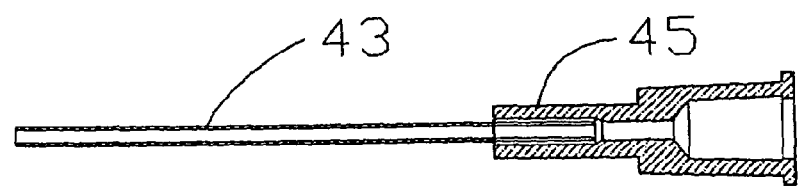
FIG. 10 is an isolated longitudinal section view of the catheter of the device shown in FIG. 1.

FIG. 10 is a longitudinal sectional view of the catheter 43 and catheter head 45.

Figure 11:
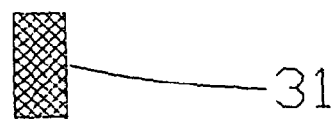
FIG. 11 is an isolated sectional view of the membrane of the device shown in FIG. 1.

FIG. 11 is an isolated sectional view of the membrane 31.

Figure 12:
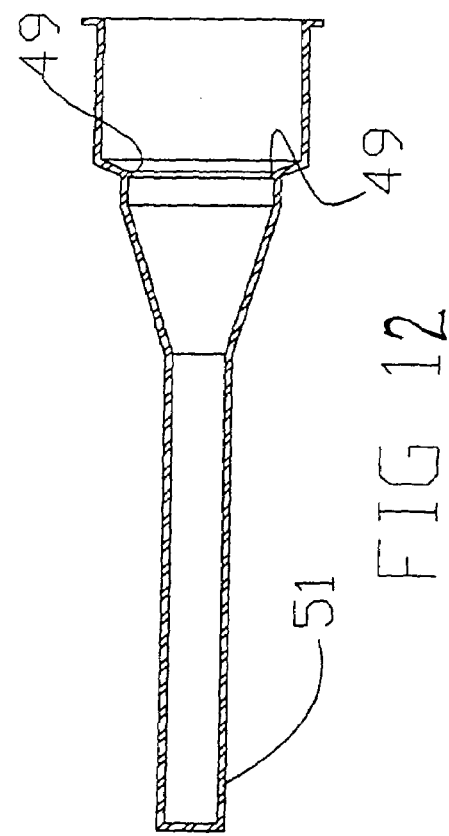
FIG. 12 is an isolated sectional view of a needle guard for use with the device shown in FIG. 1.

FIG. 12 is an isolated longitudinal sectional view of needle guard 51 illustrating guard-locking ring 49.

Figure 13:
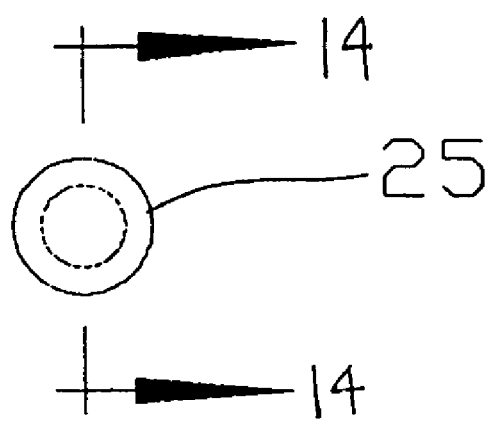
FIG. 13 is a proximal end view of the boot of the device shown in FIG. 1.
Figure 14:
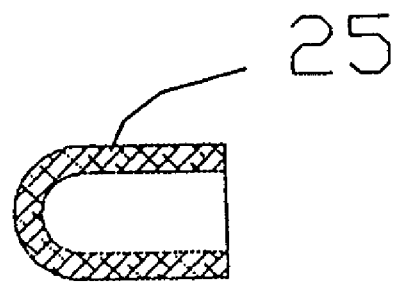
FIG. 14 is a sectional view along line 14—14 of FIG. 13.

FIG. 13 is a proximal end view of boot 25, and FIG. 14 is a sectional view along line 14—14 of boot 25.

Figure 15:
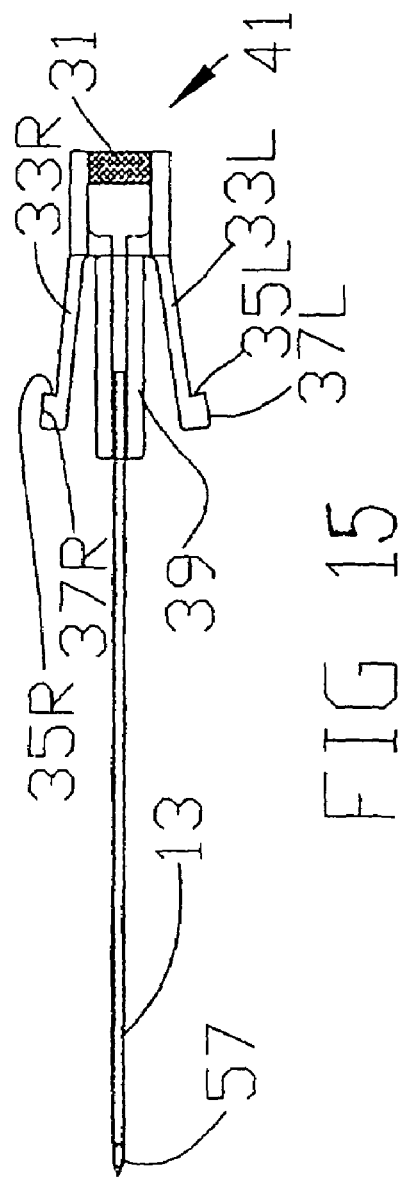

Assembly in several steps is required to produce the I-V catheter placement device 1. FIGS. 15 through 20 illustrate these steps so as to result in a finished product. With reference to FIG. 15, the first assembly step is accomplished by inserting needle 13, with its bevel 57 up, into the needle hub shaft 39 of needle hub 41. As is illustrated, this gives needle hub 41 a specific orientation, with its elemental parts having the designations shown. The membrane 31, which may be a hydrophilic medium, is inserted into the hub 41 in the properly sized space 31' provided to receive it.

Figure 16:
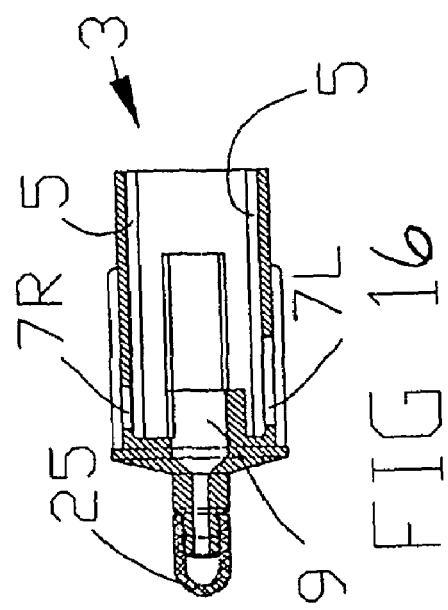

In the next step of the assembly process, boot 25 is inserted onto nose 3 as illustrated in FIG. 16. Orientation of nose 3 is determined by reference to slots 7R and 7L because slot 7L is slightly longer than slot 7R. The needle 13 and hub 41 subassembly shown in FIG. 15 are next inserted into the proximal end of nose 3, as shown in FIG. 17, by first guiding spring 15 onto needle 13. Orientation of the hub 41 and nose 3 is accomplished by insuring that catch 35R is mated with slot 7R. Once properly oriented, needle 13 is then guided through passageway 9 and projected out of nose 3, penetrating boot 25. As winged beams 33R and 33L approach nose 3, they are aligned with channel 5, flexed inward to create a spring affect along the beam, to fit the beams into channels 5 on either side of nose 3. With the winged beam 33R and 33L guided in channels 5, the needle hub 41 is forced into the nose 3 as shown in FIG. 17, until needle catch 35R pops into slots 7R. Catch 35R remains in slots 7R due to spring force of the compressed winged beam 33R and the angle of catch 35R. This process locks needle hub 41 into nose 3. Needle catch 35L floats in slot 7L. FIG. 18 shows a proximal end view of needle hub 41 fixed into nose 3.

The next step of the assembly process is attachment of body 17 to the sub-assembly of FIG. 17. As shown in FIG. 19, body 17 is aligned with the subassembly of FIG. 17 such that bevel 57 on needle 13 and orientation message 63, "USE THIS SIDE UP" on the top of body 17 face in the same direction. Once orientation is accomplished, body 17 is passed over the proximal end of nose 3, and attachment to nose 3 is accomplished by aligning and forcing slots 21 on body 17 (shown in FIG. 6) over tabs 11 on the nose 3 (shown in FIGS. 3 and 4) until they snap into position. The barrel 17 and nose 3 are mechanically keyed with side 69L being slightly wider than side 69R (shown in FIG. 4), so that they will only go together in the correct orientation.

As is illustrated in FIG. 20, assembly of the I-V catheter placement device 1 is completed by placing catheter 43 over needle 13 and sliding catheter head 45 onto boot 25 at nose 3. The catheter head 45 is held in place by light friction between the catheter head 45 and boot 25. Once the catheter 43 is in place, needle guard 51 is locked onto nose 3 by guard-locking ring 49, completing the assembly process.

As will be apparent to those of ordinary skill in the art, there are sequences of assembly other than those described that can be used to produce the completed assembly as shown in FIG. 20, producing the same I-V catheter placement device 1 ready for operation.

The sequence of operation will now be described with regard to FIGS. 21 through 27. As can be seen in FIG. 21, use of I-V catheter placement device 1 is accomplished by holding the catheter placement device 1 at its symmetrical finger grips 27 in one hand such that the hand is always behind the needle tip and orientation message 63, "USE THIS SIDE UP," is readable by the clinician, with needle 13 pointed away from the clinician. The placement site of the patient is held with the other hand behind the needle, such that the second hand is protected from possible needlestick injury. The point 59 of needle 13, with the catheter 43 concentric therewith, is inserted into the patient's vein 55 at the desired location. Verification of correct location of the catheter 43 is obtained by observation of blood "flash-back" into magnified, transparent verification cavity 53 at the top of body 17. Once proper location is confirmed, release tabs 29R and 29L, located just in front of finger grips 27, are simultaneously depressed.

As release tabs 29R and 29L are simultaneously depressed, contact pads 19R and 19L move toward their respective needle catches 35R and 35L, and an audible "click" sound is produced. Because of the design geometry, contact pad 19L moves into slot 7L, behind catch 35L, before pad 19R comes into contact with push point 37R. Continued simultaneously movement of the two release tabs causes catch 35L to become "trapped" in slot 7L between stop 67 and pad 19L, before pad 19R forces catch 35R out of the back of slot 7R. As pad 19R forces catch 35R out of slot 7R, needle hub 41, with needle 13 attached therewith, becomes unrestrained and begins to retract under force from spring 15 into the hollow of body 17. Retraction continues until catch 35L contacts pad 19L, and retraction is stopped as shown in FIG. 21. In this state, push point 37R is captured in channel 5 within nose 3, where it can no longer affect retraction of needle hub 41 into body 21.

As is shown in FIG. 22, exertion of pressure on release tabs 29R and 29L is discontinued (although the device continues to be held by the clinician by such release tabs) by the clinician and such release tabs are allowed to return to their initial, rest positions, at which time another audible "click" sound is produced. As release tab 29L returns to its rest position, pad 19L releases catch 35L. At the moment catch 35L is released by pad 19L, positive feedback between the two parts is used, increasing the lateral distance between the two parts, to obtain an unobstructed, smooth release of needle hub 41. Once released, needle hub 41, with needle 13 attached therewith, again becomes unrestrained, allowing further retraction into the hollow of body 17 under the force of spring 15.

Figure 23:
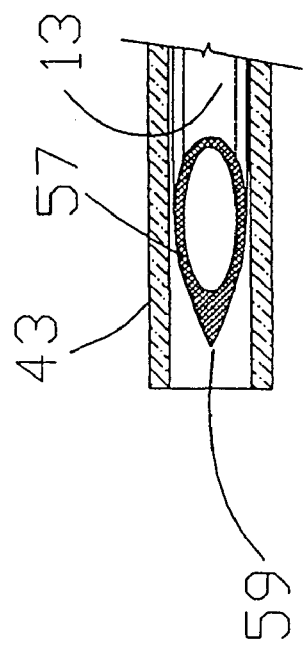

Retraction continues until catch 35L comes into contact with the back of slot 7L and all movement stops. In this state, the first stage of retraction is completed, needle tip 59 is withdrawn within catheter 43 as shown in FIG. 23, and needle hub 41 is at the fixed reference line "1" 61. Full insertion of the catheter 43 may now be completed.

Figure 24:
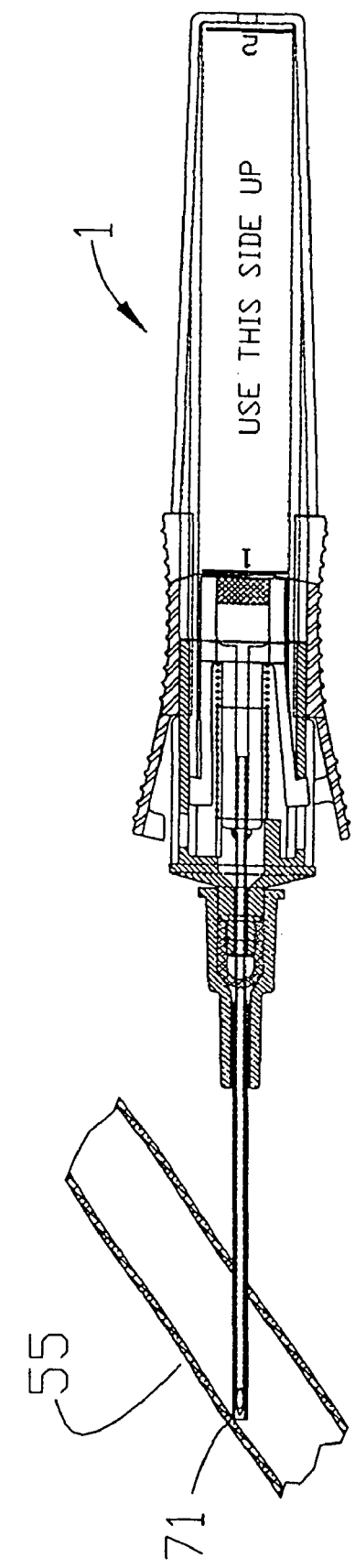

With needle tip 59 effectively blunted by catheter 43, full insertion of the catheter into the patient's vein 55, without risk of piercing the backside 71 of vein 55 ("blowing the vein") is accomplished without risk to the patient, as shown in FIG. 24.

Figure 25:
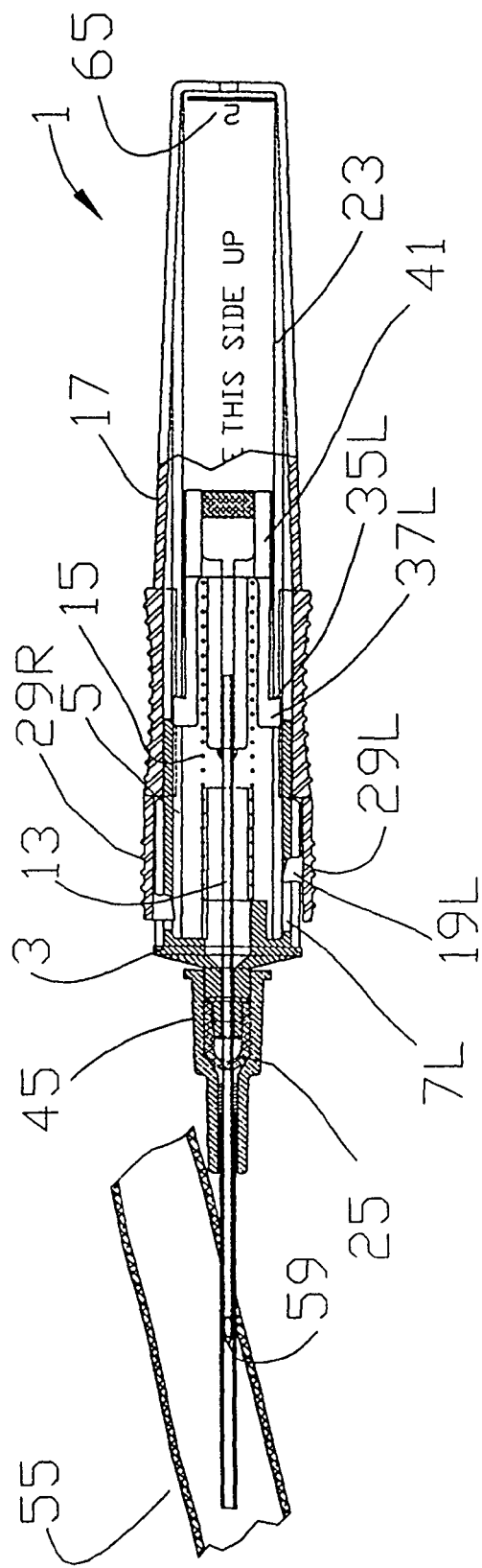

With the catheter fully inserted into the patient's vein 55 as shown in FIG. 25, second stage retraction is accomplished by simultaneously depressing release tabs 29R and 29L a second time, which produces an audible "click" sound. When this is done, no further reaction is obtained by release tab 29R, other than to balance the force required to depress the opposite release tab 29L, which adds stability for one-handed operation of the device. However, as release tab 29L moves inward, pad 19L contacts push point 37L. With continued force and movement, catch 37L is dislodged from slot 7L. When this occurs, needle hub 41, with needle 13 attached, again becomes unrestrained and is projected along channels 5 and 23, in nose 3 and body 17 respectively, into hollow 17 by the force of spring 15 as shown in FIG. 25. Needle hub 41 is then held in its retracted position at reference line "2" 65 by residual force from spring 15. As needle tip 59 passes through boot 25, the hole left in elastic boot 25 closes, preventing blood flow from the catheter into the hollow of body 17. External blood flow from the catheter at nose 3 is prevented by boot 25 being in radial contact with the internal surface of catheter head 45. With all blood flow restricted, catheter body 17 acts as a "plug" in the end of catheter head 45, until it is removed and an I-V line set is plugged into the catheter. Exertion of pressure on release tabs 29R and 29L by the clinician is discontinued (although the device continues to be held by the clinician by such release tabs), and such release tabs are allowed to return to their initial, rest positions.

Figure 26:
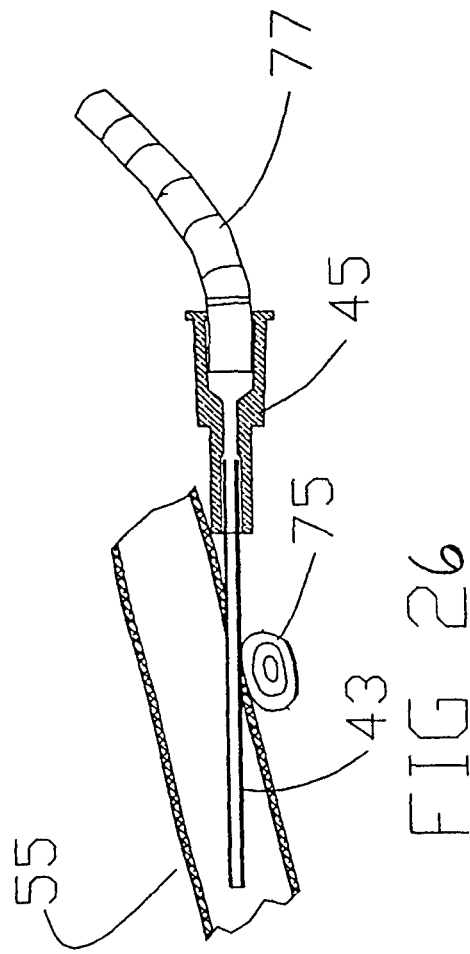
Figure 27:
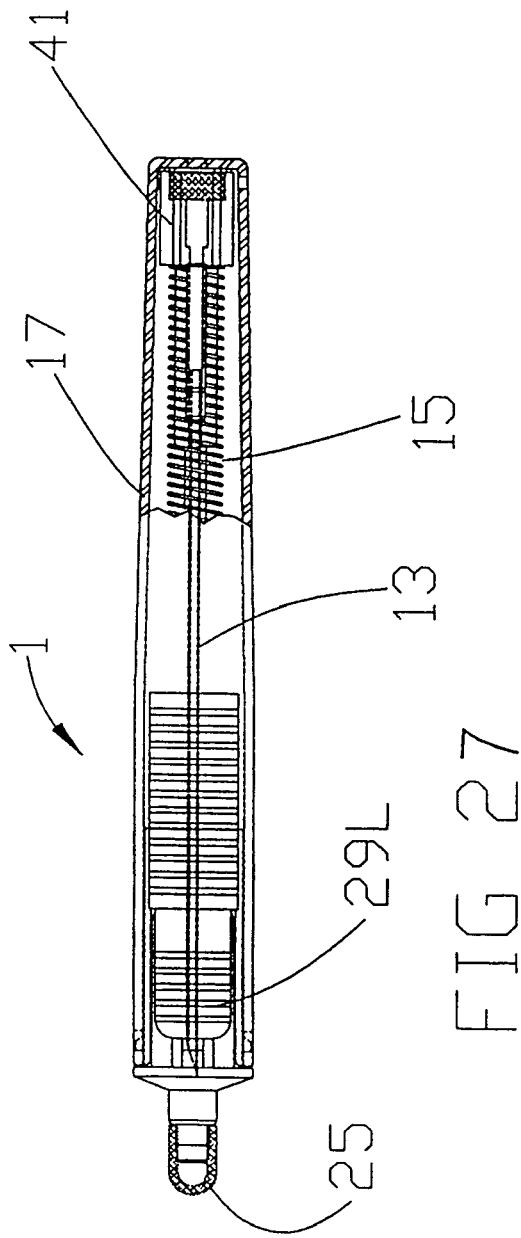

Completion of the catheter placement process is depicted in FIGS. 26 and 27. First, digital pressure 75 is applied at vein 55, where the catheter is inserted into the body. This stops blood flow from the catheter when catheter body 17 is removed. With blood flow blocked, catheter body 17 is removed and safely set aside for later disposal as shown in FIG. 27. Next, I-V line set 77 is inserted into catheter head 45. Digital pressure 75 is then removed, completing the process.

As can be understood by reference to FIGS. 21 through 27, an alternative method of needle retraction can be practiced by depressing release tabs 29R and 29L in a sequential fashion. For this method, release tab 29R is first depressed and then released. When release tab 29R is depressed, catch 35R is dislodged from the back of slot 7R. When this occurs, needle hub 41, with needle 13 attached therewith, becomes unrestrained, since catch 35L is only floating in its slot 7L. Retraction continues until catch 35L is stopped at the back of slot 7L, as shown in FIGS. 22 and 24, effectively blunting needle point 59 within catheter 43. Needle hub 41 is at reference line "1" 61.

For the second stage of needle retraction, release tab 29L is depressed and released, dislodging catch 35L from the back of slot 7L. As catch 35L is dislodged from slot 7L, needle hub 41, and the attached needle 13 are projected into hollow body 17 as previously described. Completion of the cycle occurs as previously described.

Figure 28:
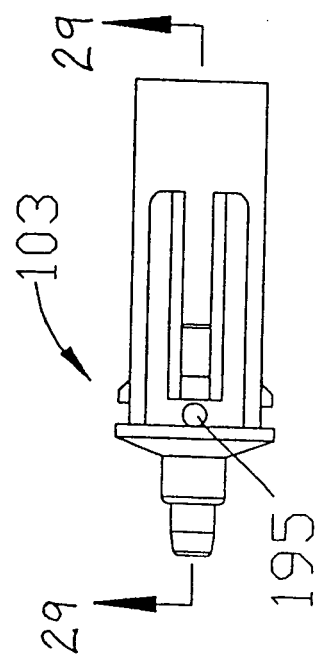
FIGS. 28–36 illustrate modified parts for an alternative embodiment of the device shown in FIG. 1.
Figure 29:
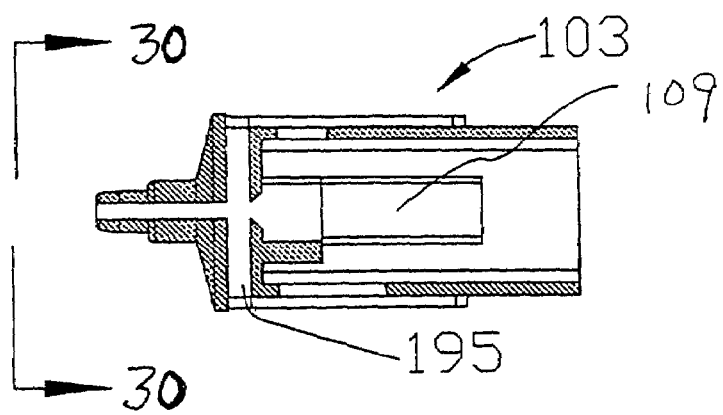
Figure 30:
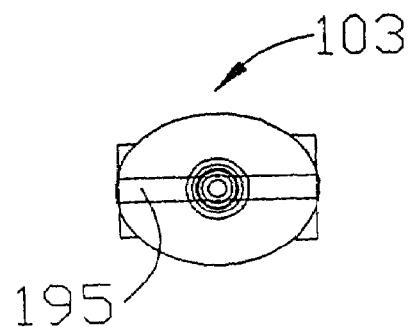
Figure 31:
Figure 32:
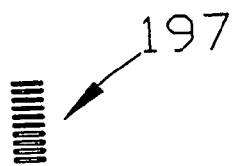
Figure 33:
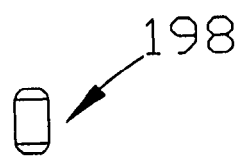
Figure 34:
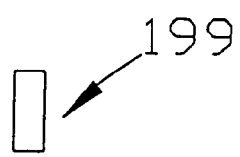
Figure 35:
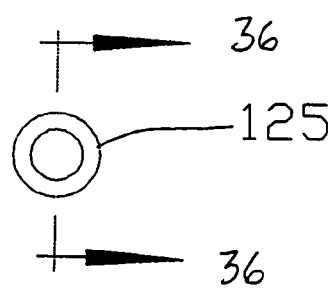
Figure 36:
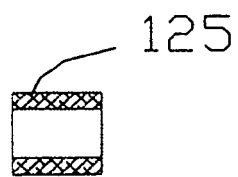

A second embodiment of this invention, catheter 101, is shown in FIG. 39. Catheter placement device 101 has a modified nose, which provides for a) an alternative flow restriction mechanism after the needle is retracted, and b) secondary locking of the retracted needle within the body of the catheter. FIGS. 28 through 42 depict the second embodiment. FIGS. 28 through 36 depict the modified parts for catheter 101. FIGS. 28, 29, and 30 illustrate nose 103 modified with through hole 195 transverse to the longitudinal axis of catheter 101. FIG. 31 is a side view of top plug 196, FIG. 32 is a side view of shuttle spring 197, FIG. 33 is a side view of shuttle 198, and FIG. 34 presents a side view of a bottom plug 199. FIG. 35 is an end view of nose seal 125, while FIG. 36 is a sectional view of nose seal 125 along line 36—36.

Figure 37:
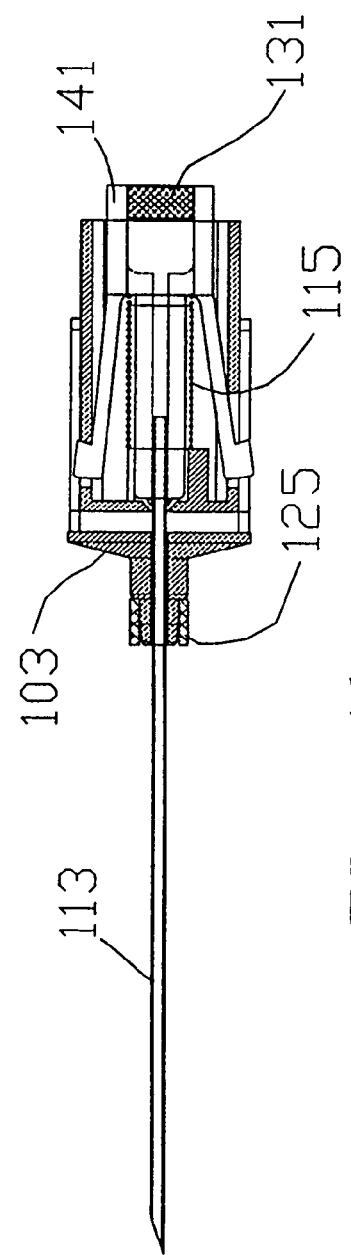
Figure 42:
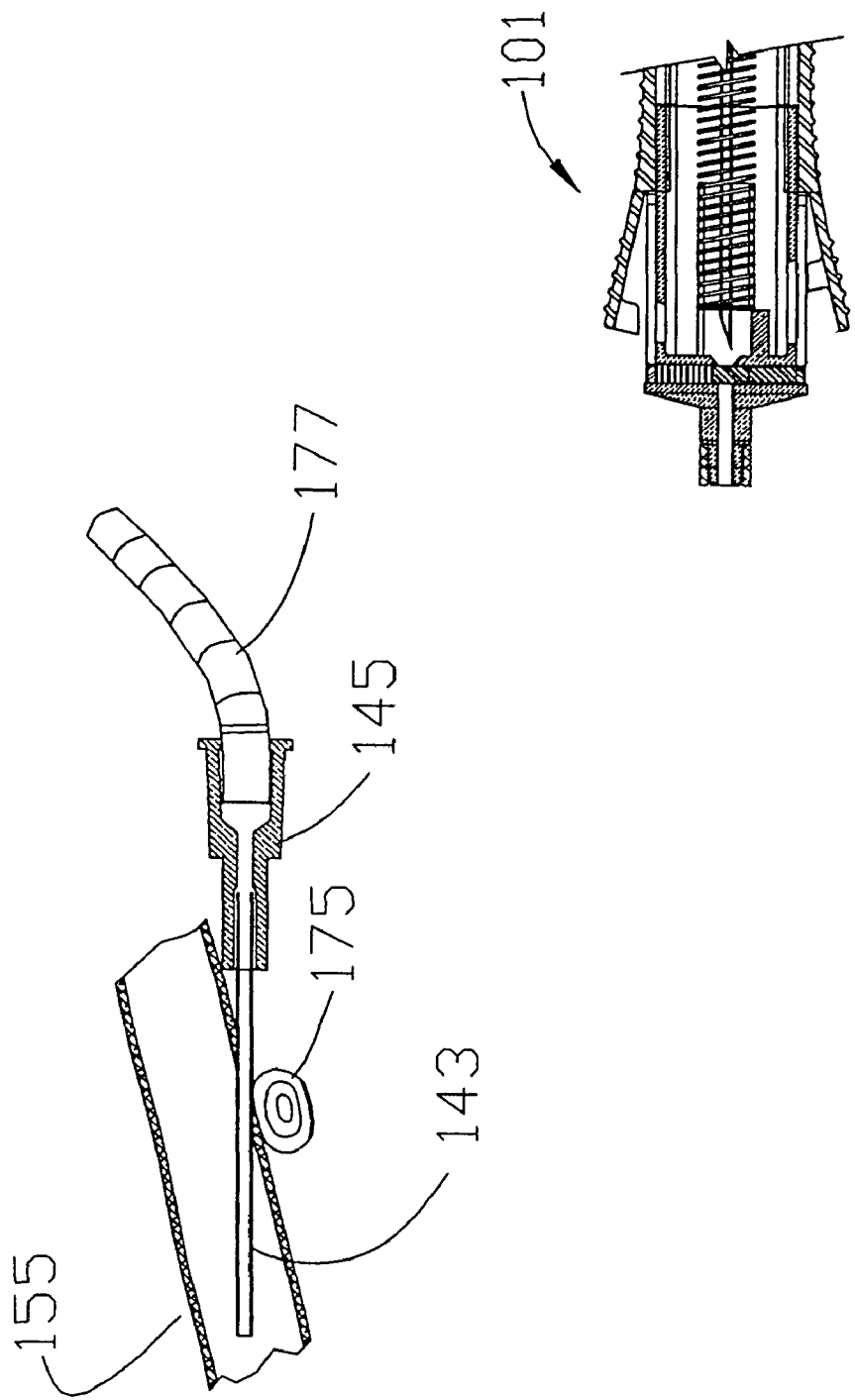

FIGS. 37–39 depict assembly of catheter 101. Needle hub 141 and needle 113 are assembled into nose 103 in the same manner as catheter 1. Nose seal 125 is inserted onto nose 103, and results in the subassembly shown in FIG. 37. With needle hub 141 and needle 113 fixed in nose 103 as shown in FIG. 38, cylindrical plug 199 is inserted into one end of through hole 195. In the other end of through hole 195, cylindrical shuttle 198 with tapers at each end, as illustrated in FIG. 33, is first inserted, followed by shuttle 198. The assembly process is completed by compressing shuttle spring 197 and inserting plug 196 into through hole 195 in nose 103 as shown in FIGS. 38 and 39. The assembly process is completed by fixing body 117 to nose 103 as in the case of catheter 1, producing catheter 101 shown in FIG. 39. As will be appreciated by reference to FIG. 40, compressed spring 197 is restrained within nose 103 by retaining plug 196 on one end and shuttle 198 at the opposite end, and applies force to one side of shuttle 198, as shown in FIGS. 38 and 39. The side of shuttle 198 opposite spring 197 is restrained in one half of through hole 195 by the shaft of needle 113 in passageway 109 of nose 103 as illustrated in FIGS. 39 and 40.

Utilization of catheter 101 is the same catheter 1. After the catheter is properly placed into the patient and release tabs 129 have been actuated to project needle 113 into the body 117 of catheter 101 as shown in FIG. 40, the point 159 of needle 113 passes shuttle 198. Once point 159 of needle 113 passes shuttle 198, shuttle 198 becomes unrestrained and is projected into passageway 109 of nose 103 by force from shuttle spring 197, thus blocking passageway 109 as illustrated in FIG. 41. The final operation is illustrated in FIG. 43, where the catheter 101 is removed from the catheter head 145 and an I-V line set 177 is inserted into catheter head 145 as described for catheter 1.

The alternate embodiments of this invention provide a novel I-V catheter placement apparatus that is operable by a single hand and that, upon completion of catheter injection, captures and encapsulates the needle and renders it harmless within the hollow of the body of the device. Alternative configurations, including one utilizing only one release tab, will become apparent to those skilled in the art from a reading of the foregoing description, which is exemplary in nature. All such modification and variations are embraced within the scope of this invention and the following claims.

What is claimed is:

1. A method for retracting an introducer needle of an intravenous catheter placement device, comprising:
    inserting a tip of the introducer needle and an intravenous catheter into a human body;
    simultaneously depressing and releasing separate release tabs of a hollow body of the an intravenous catheter placement device, thereby retracting the tip of the introducer needle inside an end of the intravenous catheter;
    inserting the intravenous catheter further into the human body; simultaneously depressing the release tabs thereby triggering an energy storage device in contact with a needle hub; and
    projecting the needle hub and needle into the hollow body and retaining the needle hub and needle in the hollow body.

2. A method for retracting an introducer needle of an intravenous catheter placement device into a hollow body, comprising:
    inserting a tip of the introducer needle with a catheter into a patient; and
    depressing a release tab affixed to the hollow body at least once, thereby triggering an energy storage device in contact with a needle hub to blunt the tip of the introducer needle into the catheter and to retract the introducer needle into the hollow body.

3. The method of claim 2, further comprising:
    orienting the hollow body such that a message on the hollow body is readable by a clinician.

4. The method of claim 3, further comprising: verifying that the catheter is inserted into the correct location by observing blood flash-back into a magnified transparent verification cavity in a needle hub.

5. The method of claim 2, further comprising:
    confirming retraction of the introducer needle by observation of an audible clicking sound when the release tabs are depressed; and
    securing the introducer needle in the hollow body by force of the energy storage device.

6. The method of claim 2, further comprising:
    eliminating blood flow from the catheter into the hollow body utilizing a boot cooperating with an interior surface of a catheter head such that blood flow is restricted from flowing back into the hollow body.

7. The method of claim 2, further comprising:
    eliminating blood flow from the catheter into the hollow body utilizing a shuttle and an energy storage device positioned in a passageway of a nose that couples to the hollow body such that when the introducer needle passes the shuttle, the shuttle becomes unrestrained and is projected into the passageway by the energy storage device and blocks the passageway, thereby restricting blood flow back into the hollow body.

8. The method of claim 2, further comprising:
    eliminating blood flow from the catheter into the hollow body utilizing a shuttle; and
    an energy storage device positioned in a passageway of a nose that couples to the hollow body.

9. A method for retracting an introducer needle of an intravenous catheter placement device into a hollow body, comprising:
    inserting a tip of the needle with a catheter into a patient;
    blunting the tip of the needle into the catheter by depressing a release tab affixed to the hollow body, thereby triggering an energy storage device in contact with a needle hub; and
    additionally depressing the release tab to trigger said energy storage device and retract the needle into the hollow body.

10. A process for placing an intravenous catheter into a human body, comprising:
    inserting an introducer needle with a catheter substantially covering the introducer needle into a human body;
    triggering an energy storage device in contact with a needle hub;
    partially retracting the introducer needle in response to said energy storage device inside an end of the catheter to blunt a tip of the introducer needle; and
    fully inserting the catheter into the human body.

11. A method for retracting an introducer needle of an intravenous catheter placement device into a hollow body comprising:
    inserting a tip of an introducer needle with a catheter into a patient;
    simultaneously depressing a release tab affixed to the hollow body at least once to blunt the tip of the introducer needle into the catheter and retract the introducer needle into the hollow body; and,
    eliminating blood flow from the catheter into the hollow body utilizing the shuttle and an energy storage device positioned in the passageway of a nose that couples the hollow body such that when the introducer needle passes the shuttle, the shuttle becomes unrestrained and is projected into the passageway by the energy storage device and blocks the passageway thereby restricting blood flow back into the body.

12. A method for retracting an introducer needle of an intravenous catheter placement device into a hollow body comprising:

inserting a tip of the introducer needle with a catheter into a patient;

depressing a release tab affixed to the hollow body at least once thereby triggering an energy storage device in contact with a needle hub to blunt the tip of the introducer needle into the catheter and retract the introducer needle into the hollow body; and, eliminating blood flow from the catheter into the hollow body utilizing a shuttle.

* * * * *